US011571380B2

(12) United States Patent
Martinez

(10) Patent No.: US 11,571,380 B2
(45) Date of Patent: Feb. 7, 2023

(54) COMPOSITIONS FOR NAIL VARNISH

(71) Applicant: FIABILA SAS, Maintenon (FR)

(72) Inventor: Francisco Martinez, Chartres (FR)

(73) Assignee: FIABILA SAS, Maintenon (FR)

( * ) Notice: Subject to any disclaimer, the term of this patent is extended or adjusted under 35 U.S.C. 154(b) by 0 days.

(21) Appl. No.: 16/077,931

(22) PCT Filed: Mar. 7, 2017

(86) PCT No.: PCT/EP2017/055262
§ 371 (c)(1),
(2) Date: Aug. 14, 2018

(87) PCT Pub. No.: WO2017/153373
PCT Pub. Date: Sep. 14, 2017

(65) Prior Publication Data
US 2019/0053998 A1 Feb. 21, 2019

(30) Foreign Application Priority Data
Mar. 8, 2016 (FR) ...................................... 1651939

(51) Int. Cl.
A61K 8/81 (2006.01)
A61K 8/25 (2006.01)
A61K 8/29 (2006.01)
A61K 8/37 (2006.01)
A61K 8/86 (2006.01)
A61Q 3/02 (2006.01)

(52) U.S. Cl.
CPC .............. A61K 8/8135 (2013.01); A61K 8/25 (2013.01); A61K 8/29 (2013.01); A61K 8/37 (2013.01); A61K 8/86 (2013.01); A61Q 3/02 (2013.01); A61K 2800/30 (2013.01)

(58) Field of Classification Search
CPC .......... A61K 8/8135; A61K 8/37; A61K 8/86; A61K 8/29; A61K 8/25; A61Q 3/02
See application file for complete search history.

(56) References Cited

U.S. PATENT DOCUMENTS

| 4,283,324 | A | | 8/1981 | Duffy | |
|---|---|---|---|---|---|
| 4,409,203 | A | | 10/1983 | Gordon et al. | |
| 5,407,666 | A | * | 4/1995 | Patel | A61K 8/8152 424/61 |
| 5,863,523 | A | * | 1/1999 | Socci | A61K 8/85 424/61 |
| 7,645,444 | B2 | | 1/2010 | Malnou et al. | |
| 8,679,465 | B2 | | 3/2014 | Malnou et al. | |
| 8,790,624 | B2 | | 7/2014 | Bonnevie | |
| 8,883,126 | B2 | | 11/2014 | Malnou | |
| 9,180,317 | B2 | | 11/2015 | Nouguerede et al. | |
| 9,211,242 | B2 | | 12/2015 | Renard et al. | |
| 2003/0152535 | A1 | | 8/2003 | Malnou et al. | |
| 2003/0165445 | A1 | | 9/2003 | Malnou et al. | |
| 2004/0022749 | A1 | | 2/2004 | Malnou | |
| 2005/0220730 | A1 | | 10/2005 | Malnou et al. | |
| 2007/0025934 | A1 | * | 2/2007 | Blin | A61K 8/86 424/61 |
| 2010/0158838 | A1 | * | 6/2010 | Kergosien | A61K 8/9789 424/61 |
| 2012/0003166 | A1 | | 1/2012 | Nouguerede et al. | |
| 2012/0014892 | A1 | | 1/2012 | Renard et al. | |
| 2012/0213718 | A1 | | 8/2012 | Bonnevie | |
| 2013/0058880 | A1 | * | 3/2013 | Dong | A61K 8/28 424/63 |
| 2014/0248225 | A1 | | 9/2014 | Renard et al. | |

FOREIGN PATENT DOCUMENTS

| DE | 102013102234 A1 | 9/2014 |
|---|---|---|
| EP | 1608322 A1 | 12/2005 |
| EP | 2248514 A2 | 11/2010 |
| FR | 2617043 A1 | 12/1988 |
| FR | 2675995 A1 | 11/1992 |
| FR | 2819176 A1 | 7/2002 |
| WO | WO-2012/123123 A2 | 9/2012 |

OTHER PUBLICATIONS

Evonik, Aerosil Product Overview, pp. 1-20, Accessed Mar. 1, 2020.*
Kowalczyk et al, International Journal of Adhesion & Adhesives, 67 (2016), pp. 44-48, Available online Dec. 2015.*
Aerosil(R) R812 Product Information, Evonik Operations GmbH, Apr. 2021 (Year: 2021).*
Database GNPD (Online) Mintel; Dec. 2003 (Dec. 2003), "Crystal Nail Varnish", XP002762343, Database accession No. 240854 the whole document.
Database GNPD (Online) Mintel; May 2007 (May 2007), "Nail Varnish", XP002762344, Database accession No. 701193 the whole document.
Database GNPD (Online) Mintel, Aug. 2002 (Aug. 2002), "Wet Look Nail Color", XP002762345, Database accession No. 10115251 the whole document.

(Continued)

Primary Examiner — Bethany P Barham
Assistant Examiner — Barbara S Frazier
(74) Attorney, Agent, or Firm — Harness, Dickey & Pierce, PLC

(57) ABSTRACT

Compositions for nail varnish, which are free or substantially free of nitrocellulose, include, in a cosmetically acceptable organic solvent:

a primary film-forming agent consisting of polyvinyl butyral, a fumed silica, at least one secondary resin, at least one plasticiser, at least one colourant, which is insoluble in said solvent.

The disclosure also relates to the use of the compositions for protecting and/or making-up the nails, as well as to packaged, ready-to-use items intended for the use.

7 Claims, No Drawings

(56) References Cited

OTHER PUBLICATIONS

Database GNPD (Online) Mintel, May 2002 (May 2002), "Water Shine Nail Varnish", XP002762346, Database accession No. 150544 the whole document.
Database GNPD (Online) Mintel, Mar. 2002 (Mar. 2002), "Wet Shine Diamonds Nail Color", XP002762347, Database accession No. 10104834 the whole document.

\* cited by examiner

COMPOSITIONS FOR NAIL VARNISH

CROSS-REFERENCE TO RELATED APPLICATIONS

This application is a National Phase Entry of International Patent Application No. PCT/EP2017/055262, filed on Mar. 7, 2017, which claims priority to French Patent Application Serial No. 1651939, filed on Mar. 8, 2016, both of which are incorporated by reference herein.

TECHNICAL FIELD

The present invention relates to new cosmetic compositions with improved properties which are more particularly useful as, or for preparing, nail varnish, said compositions being notably anhydrous and free of any nitrocellulose.

BACKGROUND

Nail varnishes have changed little since their original design. They can be used not only to adorn and beautify the nails (make-up) but also to protect them (care). In the field in question, nails obviously include both fingernails and toenails.

For the formulation of a traditional nail varnish, several conventional ingredients are used, including:

- a primary film-forming agent: this agent provides fast drying, nail adhesion, hardness and gloss. It must however be plasticised because it is brittle.
- one or more secondary resins (polymers) for improving the quality of the film: the primary film-forming agent is supplemented in commercial formulations by one or more texturing resins that make it possible to increase the dry extract and thus to control the amount of film formed on the nail surface, and thus to increase certain properties such as gloss or adhesion. The secondary resins used have long been products obtained by condensation of toluene sulphonamide and formaldehyde, and known notably under the trade name Santolite®. However, for safety reasons (high residual formaldehyde content), the latter products are increasingly being abandoned and replaced by other types of resins, for instance polyester resins, which are considered more acceptable from a cosmetic point of view.
- one or more plasticisers of the primary film-forming agent in order to optimise and modify the flexibility and pliability of the film.
- one or more usual solvents: these solvents, most often organic in nature (notably acetone, ethyl acetate or butyl acetate) are mixed with the other ingredients to form a more or less fluid composition that is easily applied on the nail with a brush. In particular, they must be capable of dissolving the film-forming agent and the secondary resins. They also allow the viscosity of the varnish to be adjusted to a suitable value. Lastly, the evaporation rate of the solvent (volatile solvent) should be neither too fast nor too slow in order to obtain the best gloss/drying compromise.
- one or more colourants: colourants that are soluble in the formulation medium are practically never used in the field of nail varnishes. On the other hand, organic and/or mineral pigments (that are insoluble in the formulation medium) authorised by regulations in cosmetic applications are used very frequently or even systematically. It is known that mineral pigments tend to promote a sedimentation phenomenon. Organic pigments, for their part, are more sensitive to chemical stability phenomena, which will be discussed below. The composition may also contain, as or in addition to the pigments, pearlescent agents and/or glitters of various natures.

For purposes of sale, nail varnish compositions prepared from the above ingredients are packaged in containers or bottles usually sealed by caps incorporating brushes for applying the product on the nail. This format and use present formulators with two particular constraints. The first difficulty is that, when the product is stored and at rest, potential sedimentation of the pigments and/or pearlescent agents within the composition should be limited to a minimum in order to maintain its homogeneity in the bottle. Stabilising colloids are often used to help control these sedimentation and physical stability phenomena. These colloids are organophilic clays (modified clays), obtained by substitution of mineral cations by organic cations from common quality clays, such as bentonite or montmorillonite. The second difficulty lies in the fact that, after removal from the bottle by a user, the nail varnish must be able to spread easily over the nail but stop flowing after application, which implies that the varnish can regain its initial viscosity once it is no longer set in motion with the brush.

Today, nitrocellulose (also commonly called "cellulose nitrate") is by far the most common primary film-forming agent used in nail varnishes. This substance indeed has many properties compatible with its application: transparency, adhesion and drying, thus making it a versatile, ubiquitous and almost universal raw material in the world of commercial nail varnishes.

However, the use of nitrocellulose is not without its disadvantages. Firstly, it is a delicate, even dangerous raw material to manufacture due to its unstable nature (highly flammable and explosive). In addition, it is prepared from cotton cellulose, by direct attack of cotton bales by a concentrated sulphonitric mixture that leads to controlled hydrolysis of the polymer and to integration of nitrogen in determined proportions. Owing to its manufacturing method, nitrocellulose thus contains residual amounts of acids (nitric acid, sulphuric acid) which can cause stability problems when the nitrocellulose comes into contact with certain types of pigments, particularly organic pigments (shade degradations).

Furthermore, nitrocellulose-based nail varnishes tend to yellow over time due to nitrocellulose degradation, thereby causing undesirable changes in the initial colour of the nail varnish. For these various reasons, many attempts have been made to substitute this film-forming agent by other systems, even if, even today, nitrocellulose, as previously mentioned, continues to be the nearly universal formulation base for commercial nail varnishes.

U.S. Pat. No. 4,283,324 describes a nail varnish composition comprising polyvinyl butyral as the primary film-forming agent, a complementary resin and an organic solvent, this composition which can be additivated with colourants and bentonite. In U.S. Pat. No. 4,409,203, it was proposed to substitute nitrocellulose by a low-molecular-weight ethyl methacrylate film-forming homopolymer. However, the varnishes described in this document prove not to adhere well to the nail, and the films thus formed are insufficiently long-lasting.

In the document FR 2 617 043, an attempt was made to substitute nitrocellulose by a film-forming copolymer resulting from copolymerisation between alkyl (meth)acrylates and hydroxyalkyl (meth)acrylates. However, it proves that with this type of film-forming agent, a softening of the film on the nail is observed as of 24 hours after application, which is disadvantageous in terms of durability and of acceptability for the consumer. In the document EP 2 248 514, it was proposed to replace nitrocellulose by a film-forming system consisting of an optionally esterified styrene-maleic acid anhydride copolymer in combination with an epoxy resin. However, the use of such a system leads to highly water-sensitive products due to the acid functions from maleic anhydride, which results in a short lifespan on the nail.

The document EP 1 608 322 describes nail varnishes containing organic fibres, such as aramid fibres ("micropulp"). It recommends the use of nitrocellulose as the primary film-forming agent ("primary resin"), and all the examples were prepared using large amounts of nitrocellulose. Examples 1 and 2 describe nail varnishes that, in addition to nitrocellulose, also contain polyvinyl butyral mixed with hydrated silica.

Lastly, the document FR 2 675 995 proposes colourless or coloured nail varnishes whose novelty is to contain, in addition to the usual ingredients (solvent, film-forming agent, resin, plasticiser, etc.), aramid fibres. The most particularly preferred film-forming agents are nitrocelluloses, and examples 1 and 3 of the document describe nail varnishes which, in addition to large amounts of nitrocellulose (more than 15% by weight), also contain polyvinyl butyral mixed with hydrated silica.

The present invention aims to solve, in whole or in part, the problems of the nail varnish compositions of the prior art, in particular those that are nitrocellulose-free. More precisely, the invention aims to propose compositions for nail varnish, which are free or substantially free of nitrocellulose, which are physically and chemically stable, in particular in terms of their colour, and which have excellent properties of use in application, notably of adhesion and of hold on the nail, as well as an excellent profile in terms of safety and of regulatory compliance. Following extensive research on this issue, it has now been found that this and other objectives can be achieved by means of a specific formulation containing a unique combination of ingredients, which provides an acceptable response to all the properties required for a nail varnish intended for commercial use, while avoiding the use of nitrocellulose.

SUMMARY

The first object of the invention is thus a composition for nail varnish, which is free or substantially free of nitrocellulose, and which includes, in a cosmetically acceptable organic solvent:
  a primary film-forming agent consisting of polyvinyl butyral,
  a fumed silica,
  at least one secondary resin,
  at least one plasticiser,
  at least one colourant, which is insoluble in said solvent.

According to an embodiment, the composition is nitrocellulose-free. According to another embodiment, the colourants are organic or mineral pigments. According to another embodiment, the fumed silica is a hydrophilic or hydrophobic fumed silica. According to another embodiment, the composition of the invention is non-aqueous.

According to a particularly preferred embodiment, the composition for nail varnish of the invention is anhydrous, nitrocellulose-free, and includes, or preferably consists of:
  a cosmetically acceptable organic solvent present in a range of 10% to 95%, preferably of 30% to 90%, and more preferentially of 50% to 85%,
  a primary film-forming agent consisting of polyvinyl butyral present in a range of 5% to 30%, preferably of 5% to 25%, more preferentially of 10% to 20%,
  a fumed silica present in a range of 0.1% to 15%, preferably of 0.3% to 10%, more preferentially of 0.5% to 5%,
  at least one secondary resin present in a range of 1% to 20%, preferably of 3% to 20%, more preferentially of 5% to 15%,
  at least one plasticiser present in a range of 0.1% to 10%, preferably of 0.5% to 8%, more preferentially of 0.5% to 6%,
  at least one pigment present in a range of 0.001% to 15%, preferably of 0.005% to 12%, more preferentially of 0.01% to 10%,
the above percentages being expressed by weight relative to the total composition.

The invention has many advantages: the nail varnishes can be totally nitrocellulose-free; they are perfectly stable chemically (no degradation and/or colour change) and physically (no sedimentation); they are extremely easy to apply; and the films obtained on the nail after drying have excellent qualities.

A second object relates to the use of the compositions of the invention for protecting and/or making-up the nails. A third object relates to a method for protecting and/or making-up the nails, which essentially consists in applying to the latter a composition of the invention. Lastly, a final object relates to packaged, ready-to-use items containing the composition of the invention.

DETAILED DESCRIPTION

The invention will now be described in greater detail and in a non-limiting manner in terms of the various aspects of which it is composed.

Organic Solvent

The composition for nail varnish of the invention includes at least one organic solvent for solubilising the polymeric substances contained therein. This solvent may thus be selected from:
  ketones that are liquid at room temperature such as methylethyl ketone, acetone, methylisobutyl ketone;
  alcohols that are liquid at room temperature such as ethanol, propanol, butanol, isopropanol, diacetone alcohol;
  short-chain esters with 3 to 8 carbon atoms such as ethyl acetate, propyl acetate, butyl acetate;
  alkanes that are liquid at room temperature such as heptane, dodecane, hexane;
  and mixtures thereof.

Preferably, the solvent medium is anhydrous or substantially anhydrous, i.e., the composition is ultimately in a non-aqueous or substantially non-aqueous form, i.e., with a water content by weight of less than 1%. The organic solvent or solvent mixture is preferably present in the composition in an amount comprised between 10% and 95% by weight, preferably between 30% and 90% by weight, and more preferentially between 50% and 85% by weight, relative to the total weight of the composition.

Primary Film-Forming Agent

The composition for nail varnish of the invention includes a primary film-forming agent which consists of polyvinyl butyral. Polyvinyl butyral, also called poly(vinyl butyral), is a synthetic thermoplastic polymer used, among other purposes, to assemble glasses and to manufacture laminated glass. Polyvinyl butyral can be prepared from vinyl acetate which, by radical polymerisation, becomes polyvinyl acetate. Polyvinyl acetate is then hydrolysed to form polyvinyl alcohol in the presence of an acid catalyst. Polyvinyl alcohol then undergoes an acetalisation reaction in the presence of butanal (butyraldehyde) in the presence of acid to form polyvinyl butyral. Polyvinyl butyral is a commercially available product, sold notably by the company Kuraray under the name Mowital®.

According to an embodiment, the composition for nail varnish of the invention may include, in addition to the primary film-forming agent, one or more complementary film-forming polymers known per se, such as for example a polyester resin or a tosylamide epoxy resin. According to another embodiment, the composition contains no film-forming agent other than polyvinyl butyral polymer.

The primary film-forming polymer consisting of polyvinyl butyral advantageously has an average molecular mass comprised between 10,000 and 100,000 g/mol and preferably between 15,000 and 60,000 g/mol. According to a preferred embodiment, the primary film-forming polymer consisting of polyvinyl butyral has a glass-transition temperature Tg ranging from 40° C. to 100° C., preferably from 60° C. to 80° C. The amount of primary film-forming agent consisting of polyvinyl butyral in the composition for nail varnish of the invention may be from 5% to 30% by weight, preferably from 5% to 25%, more preferentially from 10% to 20%, relative to the total weight of the composition.

According to the invention, the composition is free, or substantially free, of nitrocellulose. "Substantially" means a nitrocellulose concentration of less than, or not exceeding, 5,000 ppm, preferably of less than 1,000 ppm, more preferentially of less than 500 ppm, and even more preferentially of less than 100 ppm.

Secondary Resin

The composition for nail varnish of the invention further includes at least one secondary resin. This secondary resin, which may or may not have film-forming properties, may be selected from acrylic resins, styrene acrylic resins, polyester resins, alkyd resins, polyurethane resins, ketone resins, tosylamide epoxy resins, epoxy resins, polyamide resins, polyvinyl acetate resins, and mixtures thereof. The use of these resins is well known in the field of cosmetics, especially in the field of nail varnishes. Examples include the following commercially available resins: Elvacite® 2046 from the company Lucite (acrylic resin), Beckosol® OD 230-70-E from Dainippon (alkyd resin), Trixene® PR 4127 from Baxenden (polyurethane resin), Variplus® SK from Tego (ketone resin) and Polytex® NX 55 from Estron Chemical (tosylamide epoxy resin).

Secondary resin means one or more polymer(s) in a lower proportion by weight than the primary film-forming agent consisting of polyvinyl butyral. In a nail varnish formulation, the main function of a secondary resin is to increase gloss and nail adhesion. The amount of secondary resin(s) in the composition for nail varnish of the invention may range from 1% to 20% by weight, preferably from 3% to 20%, more preferentially from 5% to 15%, relative to the total weight of the composition.

Plasticiser

The composition for nail varnish of the invention also includes at least one plasticiser. In a way known in the field, the function of the plasticiser is to allow the hardness/flexibility compromise of the film to be adjusted. According to the invention, the plasticiser may thus be selected, alone or in mixture, from:
  esters of acids, notably carboxylic acids, such as citrates, benzoates, adipates and carbonates;
  isosorbide diesters.

Isosorbide is a product obtained by dehydration of a glucose derivative, sorbitol, which can be extracted from rowan berries or from cereals. The diester is advantageously produced by reaction between a fatty acid of vegetable origin and isosorbide. Examples of citrate esters include triethyl citrate, tributyl citrate, tributyl acetylcitrate. And, an example of a benzoate ester is trimethyl pentanediol dibenzoate. The plasticiser is advantageously present in the composition for nail varnish in a concentration comprised between 0.1% and 10% by weight, preferably between 0.5% and 8%, more preferentially between 0.5% and 6%, by weight relative to the total weight of the composition.

Fumed Silica

The composition for nail varnish of the invention includes fumed silica. According to an embodiment, the fumed silica is selected from hydrophilic fumed silicas and hydrophobic fumed silicas. Preferably, fumed silicas having a hydrophobic nature are used.

Hydrophilic fumed silicas can be obtained by high-temperature hydrolysis of a volatile silicon compound in an oxyhydrogen flame, producing a finely divided silica. Hydrophilic silicas have a large number of silanol groups on their surfaces. Such hydrophilic silicas are marketed under the names "AEROSIL® 200", "AEROSIL® 300" by the company Evonik, for example.

Hydrophobic fumed silicas can be obtained by modifying the surface of the silica by a chemical reaction that decreases the number of silanol groups, these groups which may be substituted by hydrophobic groups. The hydrophobic groups may be:
  trimethylsiloxyl groups, which are notably obtained by treatment of fumed silica in the presence of hexamethyldisilazane. Silicas treated in this way are called "silica silylate" according to the CTFA ($6^{th}$ edition, 1995). They are marketed by Evonik under the product designation "AEROSIL® R812", for example.
  dimethylsilyloxyl or polydimethylsiloxane groups, which are notably obtained by treatment of fumed silica in the presence of polydimethylsiloxane or dimethyldichlorosilane. Silicas treated in this way are called "silica dimethyl silylate" according to the CTFA ($6^{th}$ edition, 1995). They are marketed by Evonik under the product designation "AEROSIL® R972", for example.

Fumed silicas (hydrophilic or hydrophobic) generally have high specific surface areas (measured according to the BET method), in particular higher than 30 $m^2/g$, and more particularly higher than 100 $m^2/g$. According to the invention, it is preferred to use fumed silicas whose specific surface area is comprised between 50 $m^2/g$ and 380 $m^2/g$, and more advantageously between 200 $m^2/g$ and 300 $m^2/g$. Fumed silica may be present in the composition for nail varnish in a content comprised between 0.1% and 15% by weight, preferably between 0.3% and 10%, more preferentially between 0.5% and 5%, by weight relative to the total weight of the composition.

Colourant

The composition for nail varnish of the invention further includes at least one colourant selected for example from pigments, pearlescent agents and glitters. Pigments should be understood to mean particles of any shape, white or coloured, mineral or organic, natural or synthetic, insoluble in the formulation medium (solvent), and intended to add colour to the composition.

Pearlescent agents should be understood to mean iridescent particles of any shape, notably produced by certain molluscs in their shell or synthesised. The main pearlescent agent substrates are as follows: natural mica, fluorophlogopite, borosilicate, aluminium, etc. These substrates are then coated either with titanium dioxide alone, which corresponds to iridescent white pearlescent agents, or with different layers of mineral pigments (titanium dioxide, iron oxide, iron ferrocyanide, etc.) and organic pigments (such as Red 7, Red 34, Yellow 5, etc.).

With regard to glitters, the main substrates are polyethylene terephthalate and polybutylene terephthalate. The resins used to coat the thin aluminium layer and/or to colour the glitter are based on polyurethane 11, polyurethane 33, acrylic copolymer or vinyl acetate/ethylene copolymer.

The pigments may be white or coloured, mineral and/or organic. Examples of mineral pigments include titanium dioxide, zirconium or cerium oxides, zinc oxides, chromium oxides, various shades of iron oxide (black, yellow or red), ultramarine blue, iron ferrocyanide, manganese violet, etc. Examples of organic pigments more particularly include Red 7, Red 34, Yellow 5, and more generally insoluble D&C pigments. Pearlescent pigments may be in the form, for example, of mica or borosilicate particles coated with one or more layers of titanium oxide and/or iron oxide which, by reflecting and refracting light, impart reflective properties to the varnish in the dry state.

The pigment, or the mixture of pigments, is preferably present in the composition in an amount comprised between 0.001% and 15% by weight, preferably between 0.005% and 12% by weight, more preferentially between 0.01% and 10% by weight, relative to the total weight of the composition. The compositions of the invention may optionally contain, in addition to the above-mentioned insoluble colourants, one or more colourants that would be soluble, at least partly, in the cosmetically acceptable solvent used.

Optional Additives

In addition to the essential ingredients defined above, the composition of the invention may, optionally, further contain complementary additives customary in the field of cosmetics, such as, for example, anti-UV agents, antioxidants, surfactants such as silicones, fragrances, or active agents such as vitamins, proteins or plant extracts.

Preparation of the Compositions of the Invention

The compositions of the invention can be prepared according to conventional methods well-known to persons skilled in the field of nail varnish formulation. Furthermore, methods for preparing these compositions are illustrated in the examples given below.

Packaged Items and Use of the Compositions of the Invention

The compositions of the invention can be packaged in any type of containers or bottles known per se, for example made of glass or plastic, provided at one end with a removable opening and closing system (such as a screw on/off cap), thereby providing sealing for good preservation. The caps can be provided with an applicator (brush, spatula, tip) which, after dipping in the composition, allows said composition to be applied on the nail. According to another variant, the applicator is not integral with the cap and constitutes a separate item so as to form a two-part container/applicator kit.

Before use, the viscosity of the packaged composition (at rest) is generally comprised between 1,500 and 3,000 cP (according to the Brookfield measurement specified in the examples). At the time of use, after mechanical shaking and/or dipping of the applicator, the viscosity of the composition drops to then be generally comprised between 400 and 1,500 cP (according to the Brookfield measurement specified in the examples), so as to allow its flawless application on the nail by the user. After application on the nail, the composition gradually regains its initial viscosity and dries (at room temperature and/or by applying heat to accelerate drying), so as to ultimately form a continuous and long-lasting film coating on the nail. If the user so desires, the nail varnish film can then be removed with a conventional nail varnish remover, such as ethyl acetate.

EXAMPLES

Products in accordance with the invention and comparative products were prepared. The following raw materials were used to prepare these products:

Mowital®: polyvinyl butyral (primary film-forming agent) marketed by Kuraray

CAB 381-0.5®: ester acetate/cellulose butyrate (primary film-forming agent) marketed by Eastman Polytex E75®: secondary tosylamide epoxy resin marketed by Estron Chemical Aerosil R812®: hydrophobic fumed silica marketed by Evonik Sorbosil BFG50®: hydrated silica marketed by PQ Corporation Tixogel MP Z®: hydrophobic bentonite marketed by BYK Uvasorb 20H®: organic UV filter (benzophenone-1) marketed by 3V The following tests were performed on the prepared products:

Gloss: a 100-µm thick layer of the varnish composition is applied to a Leneta plate. After the film obtained is dried at 20° C., its gloss (GU) is measured at an angle of incidence of 60° using a BYK-Gardner glossmeter.

Hardness: the "Persoz" hardness is measured on a glass plate coated with a 100-µm wet varnish (according to ISO1522). A minimum value of 200 is desired, preferentially higher than 210.

Adhesion: the "cross-hatch test" is performed on a glass plate. A 100-µm wet film is applied and dried 24 hours at 20° C. Cross-hatching is made using a multiple-blade knife. Adhesive tape is applied to this cross-hatching, then pulled off: the cross-hatching is then analysed. A score of 0 corresponds to no loss of adhesion (no squares were removed). A score of 5 corresponds to total loss of adhesion (all squares were removed). A score between 0 and 1 is essential.

Stability: A shade containing one or more organic pigments is prepared. A 400-µm-thick film is prepared on a card and dried. This film is analysed using a spectrophotocolorimeter. After 24 hours at 20° C., a new film is applied and analysed in the same way as before. Comparison of the values of L, a, b provides information about changes in the colour over time.

Viscosity: measured with a Brookfield DVIII+ viscometer using spindle no. 3. The sample to be measured is placed in a 25° C. temperature-controlled bath for 12 hours. The spindle is then introduced into this sample and the viscosity measurement is performed at a speed of 60 rpm.

First manufacturing step: manufacture of products in gel form (produced with no plasticiser or pigment).

Compositions:

| Example No. | 1 | 2 | 3 | 4 | 4A |
|---|---|---|---|---|---|
| Butyl acetate | 74 | 73 | 74 | 73 | 74 |
| Polytex E75 | 10 | 10 | 10 | 10 | 10 |
| Aerosil R812 | 7 | 0 | 7 | 0 | 0 |
| Tixogel MP Z | 0 | 6 | 0 | 6 | 0 |
| Sorbosil BFG50 | 0 | 0 | 0 | 0 | 7 |
| Mowital 30HH | 9 | 9 | 0 | 0 | 9 |
| CAB 381-0.5 | 0 | 0 | 9 | 9 | 0 |
| Diacetone alcohol | 0 | 1 | 0 | 1 | 0 |

The product of example 1 has a formulation scheme in accordance with the invention (polyvinyl butyral+fumed silica), the other examples being comparative.

Manufacturing Method:
Load butyl acetate and either Aerosil R812 or Tixogel MP Z or Sorbosil BFG50 into a 2-L beaker. Deagglomerated it by stirring. Incorporate Polytex E75 with stirring. Stir for 20 minutes. Introduce diacetone alcohol if necessary. Introduce Mowital 30HH or CAB 381-0.5, depending on the formula, and stir for 10 minutes. Grind the mixture obtained in a ball mill. A gel is thus obtained.

The viscosity and gloss of the products thus prepared was measured:

| Example No. | 1 | 2 | 3 | 4 | 4A |
|---|---|---|---|---|---|
| Viscosity (60 rpm, 25° C.) | 2500 | 9200 | 9200 | 8700 | 200 |
| Gloss (60°) | 48.5 | 58.1 | 24.6 | 64.1 | 32 |

For product 4A, silica sedimentation was observed.

Second manufacturing step: manufacture of varnish bases (with no pigment).

Compositions:

| Example No. | 5 | 6 | 7 | 8 | 8A |
|---|---|---|---|---|---|
| Butyl acetate | 22.8 | 22.77 | 22.8 | 22.77 | 22.77 |
| Ethyl acetate | 35 | 35 | 35 | 35 | 35 |
| Mowital 30HH | 9 | 9 | 0 | 0 | 9 |
| Mowital 60HH | 3 | 3 | 0 | 0 | 3 |
| CAB 381-05 | 0 | 0 | 12 | 12 | 0 |
| Uvasorb 20H | 0.2 | 0.2 | 0.2 | 0.2 | 0.2 |
| Acetyl tributyl citrate | 1 | 1 | 3 | 3 | 1 |
| Polytex E75 | 9 | 9 | 9 | 9 | 9 |
| Gel Example 1 | 20 | 0 | 0 | 0 | 0 |
| Gel Example 2 | 0 | 20 | 0 | 0 | 0 |
| Gel Example 3 | 0 | 0 | 20 | 0 | 0 |
| Gel Example 4 | 0 | 0 | 0 | 20 | 0 |
| Gel Example 4A | 0 | 0 | 0 | 0 | 20 |
| Phosphoric acid | 0 | 0.03 | 0 | 0.03 | 0 |

The product of example 5 has a formulation scheme in accordance with the invention (polyvinyl butyral+fumed silica), the other examples being comparative.

Manufacturing Method:
Load butyl acetate and ethyl acetate into a 2-L beaker. With stirring, introduce Mowital 30HH then Mowital 60HH or CAB 381-0.5, depending on the formula. Once solubilised, introduce Uvasorb 20H, Polytex E75, acetyl tributyl citrate and, depending on the formula, the gel of preceding examples 1 to 4A. Stir for 15 minutes. If necessary, add phosphoric acid and stir the mixture for an additional 15 minutes. A varnish base is obtained with the following features:

| Example No. | 5 | 6 | 7 | 8 | 8A |
|---|---|---|---|---|---|
| Brookfield viscosity (60 rpm, 25° C., mPa · s) | 700 | 690 | 900 | 760 | 400 |
| Gloss (60°) | 89 | 90.2 | 70.8 | 87.4 | 50 |
| Hardness | 289 | 282 | 240 | 225 | — |
| Adhesion | 0 | 0 | 5 | 0 | 5 |

Manufacture of Finished Products and Evaluation of Colour Stability and of Hold on the Nail In order to produce shades, it was first necessary to grind the pigments. The following compositions were prepared:

| Example No. | 9 | 10 | 11 | 12 |
|---|---|---|---|---|
| Butyl acetate | 17 | 17 | 27 | 27 |
| Ethyl acetate | 19 | 19 | 29 | 29 |
| Isopropanol | 3 | 3 | 5 | 5 |
| Polytex E75 | 6 | 6 | 10 | 10 |
| Mowital 30HH | 7 | 0 | 11 | 0 |
| CAB 381-0.5 | 0 | 7 | 0 | 11 |
| Acetyl tributyl citrate | 8 | 8 | 8 | 8 |
| Titanium dioxide | 40 | 40 | 0 | 0 |
| Red 34 | 0 | 0 | 10 | 10 |

Load butyl acetate, ethyl acetate and isopropanol into a 2-L beaker. Incorporate Polytex E75 and Mowital 30HH or CAB 381-0.5, depending on the formula, with stirring. Once the Mowital dissolves, add the pigment and stir for 30 minutes. Grind the mixture obtained in a ball mill. A colourant solution is then obtained.

The following shade was then produced as a finished product to show the improvement in colour stability.

| Example No. | 13 | 14 | 15 | 16 | 16A |
|---|---|---|---|---|---|
| Example composition 5 | 97.9 | 0 | 0 | 0 | 0 |
| Example composition 6 | 0 | 97.9 | 0 | 0 | 0 |
| Example composition 7 | 0 | 0 | 97.9 | 0 | 0 |
| Example composition 8 | 0 | 0 | 0 | 97.9 | 0 |
| Example composition 8A | 0 | 0 | 0 | 0 | 97.9 |
| Example composition 9 | 2 | 2 | 0 | 0 | 2 |
| Example composition 10 | 0 | 0 | 2 | 2 | 0 |
| Example composition 11 | 0.1 | 0.1 | 0 | 0 | 0.1 |
| Example composition 12 | 0 | 0 | 0.1 | 0.1 | 0 |

Only the product of example 13 corresponds to a product in accordance with the invention, the other examples corresponding to comparative products (because fumed silica was substituted by bentonite and/or hydrated silica and/or because polyvinyl butyral was substituted by a cellulose ester). All products have the same colourant system, namely a $TiO_2$+Red 34 mixture, at the same concentration.

A colour measurement (L, a, b system) was performed at T0 and T+24 h on the products thus prepared. The following results were obtained:

| Example No. | 13 | 14 | 15 | 16 | 16A |
|---|---|---|---|---|---|
| L | 76.46 | 76.54 | 75.14 | 75.01 | 76.85 |
| L + 24 h | 76.98 | 76.10 | 75.39 | 74.8 | 75.16 |
| a | 22.61 | 23.53 | 24.26 | 24.04 | 21.41 |
| a + 24 h | 22.04 | 30.48 | 24.21 | 35.28 | 23.54 |
| b | −8.99 | −8.56 | −10.02 | −10.28 | −10.21 |
| b + 24 h | −8.63 | −5.09 | −9.79 | −8.04 | −10.56 |

Very little difference in the variation of the 3 colour components is observed between the measurement at T0 and the measurement after 24 hours for examples 13 and 15. For examples 14 and 16, this variation is very strong. A bluish pink turns to a yellow pink. For example 16A, a decrease in L (which corresponds to a loss of white) and an increase in a (which corresponds to an increase in red) is observed. This is due to the inability of hydrated silica to stabilise the pigments: titanium dioxide sedimentation, and thus a less white, redder shade, is observed.

The hold of the varnishes on the nail was then evaluated. To this end, an in vivo test was conducted on a panel of 20 people. These panellists gave their opinion on the hold of the varnish applied on the nail, by indicating the number of days this hold was observed. The average of the responses is presented in the table below:

| Example No. | 13 | 14 | 15 | 16 |
|---|---|---|---|---|
| Noted number of days of hold on the nail (average) | 4.8 | 4.3 | 1.4 | 1.8 |

A very poor hold on the nail, indeed not exceeding 2 days, was observed for varnishes 15 and 16. In contrast, varnishes 13 and 14 have a very good hold of nearly 5 days.

To finish, the following measurements were performed on the compositions of examples 13 to 16:

| Example No. | 13 | 14 | 15 | 16 |
|---|---|---|---|---|
| Brookfield viscosity (60 rpm, 25° C., mPa · s) | 900 | 780 | 960 | 620 |
| Gloss (60°) | 86.9 | 86.4 | 52.9 | 78.3 |
| Hardness | 267 | 263 | 225 | 204 |
| Adhesion | 0 | 0 | 5 | 0 |

In conclusion, it can therefore be observed that the nail varnish of example 13, which is in accordance with the invention, is the one that has the best properties in terms of both colour stability and hold on the nail. Furthermore, this nail varnish also has very good properties of gloss, hardness and adhesion (as also shown for example 5).

The invention claimed is:

1. A composition for nail varnish free or substantially free of nitrocellulose, the composition comprising:
   an organic solvent selected from the group consisting of: butyl acetate, ethyl acetate, and combinations thereof;
   a primary film-forming agent consisting of polyvinyl butyral having an average molecular mass ranging from 10,000 g/mol to 100,000 g/mol;
   a fumed silica, the fumed silica being hydrophobic;
   at least one secondary resin comprising tosylamide epoxy resin;
   at least one plasticiser comprising citrate ester; and
   at least one colourant that is insoluble in the solvent,
   the organic solvent representing from 50% to 85% of a total weight of the composition,
   the primary film-forming agent representing from 10% to 20% of the total weight of the composition,
   the fumed silica representing from 0.5% to 5% of the total weight of the composition,
   the at least one secondary resin representing from 5% to 15% of the total weight of the composition,
   the plasticizer representing from 0.5% to 6% of the total weight of the composition, and
   that at least one colourant representing from 0.01% to 10% of the total weight of the composition.

2. The composition of claim 1, wherein the composition is anhydrous or substantially anhydrous.

3. The composition of claim 1, wherein the polyvinyl butyral has an average molecular mass ranging from 15,000 g/mol to 60,000 g/mol.

4. The composition of claim 1, wherein the polyvinyl butyral has a glass-transition temperature Tg ranging from 40° C. to 100° C.

5. The composition of claim 1, wherein the fumed silica has a specific surface area comprised between 50 m$^2$/g and 380 m$^2$/g.

6. The composition of claim 1, wherein the colourant is an organic or mineral pigment.

7. An item comprising:
   (i) a container provided with a closure system and filled with a nail varnish composition, the nail varnish composition comprising:
      an organic solvent selected from the group consisting of: butyl acetate, ethyl acetate, and combinations thereof;
      a primary film-forming agent consisting of polyvinyl butyral having an average molecular mass ranging from 10,000 g/mol to 100,000 g/mol;
      a hydrophobic fumed silica;
      at least one secondary resin comprising tosylamide epoxy resin;
      at least one plasticiser comprising citrate ester; and
      at least one colourant that is insoluble in the organic solvent,
      the organic solvent representing from 50% to 85% of a total weight of the composition,
      the primary film-forming agent representing from 10% to 20% of the total weight of the composition,
      the at least one secondary resin representing from 5% to 15% of the total weight of the composition,
      the fumed silica representing from 0.5% to 5% of the total weight of the composition,
      the plasticizer representing from 0.5% to 6% of the total weight of the composition, and
      that at least one colourant representing from 0.01% to 10% of the total weight of the composition; and
   (ii) an applicator configured to, after dipping in the container, deposit the composition on a nail.

\* \* \* \* \*